US012600932B2

(12) United States Patent
Alagur et al.

(10) Patent No.: US 12,600,932 B2
(45) Date of Patent: Apr. 14, 2026

(54) BIOPROCESSING PERFUSION SYSTEM HAVING A PLURALITY OF FILTERS AND METHOD OF OPERATING THE SAME

(71) Applicant: GLOBAL LIFE SCIENCES SOLUTIONS USA LLC, Marlborough, MA (US)

(72) Inventors: Sahebagouda Alagur, Bengaluru (IN); Prashanth Hosabettu Mohan, Bengaluru (IN); Praveen Paul, Bengaluru (IN)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 699 days.

(21) Appl. No.: 17/998,331

(22) PCT Filed: Jul. 13, 2021

(86) PCT No.: PCT/EP2021/069517
§ 371 (c)(1),
(2) Date: Nov. 9, 2022

(87) PCT Pub. No.: WO2022/013248
PCT Pub. Date: Jan. 20, 2022

(65) Prior Publication Data
US 2023/0212499 A1      Jul. 6, 2023

(30) Foreign Application Priority Data

Jul. 15, 2020    (IN) .............................. 202041030186

(51) Int. Cl.
*C12M 1/00*        (2006.01)
*B01D 61/14*       (2006.01)
(Continued)

(52) U.S. Cl.
CPC ........... *C12M 29/10* (2013.01); *B01D 61/149* (2022.08); *C12M 29/04* (2013.01); *C12M 41/32* (2013.01);
(Continued)

(58) Field of Classification Search
CPC ...... C12M 29/10; C12M 29/04; C12M 41/32; C12M 41/40; C12M 41/48; C12M 47/10; B01D 61/149; B01D 2317/04
See application file for complete search history.

(56) References Cited

U.S. PATENT DOCUMENTS

| | | | |
|---|---|---|---|
| 12,195,715 B2 * | 1/2025 | Paul ........................ | B01D 61/22 |
| 2015/0158907 A1 * | 6/2015 | Zhou ....................... | C12M 41/00 |
| | | | 530/399 |

(Continued)

FOREIGN PATENT DOCUMENTS

| | | | |
|---|---|---|---|
| CA | 2838737 A1 | 12/2012 | |
| EP | 3012012 A1 | 4/2016 | |
| WO | WO-2020058509 A1 * | 3/2020 | ............ C12M 29/04 |

OTHER PUBLICATIONS

PCT International Search Report and Written Opinion for PCT/EP2021/069517, mailed Dec. 23, 2021 (12 pages).
(Continued)

*Primary Examiner* — Michael L Hobbs
(74) *Attorney, Agent, or Firm* — Eversheds-Sutherland (US) LLP

(57)        ABSTRACT

The bioprocessing perfusion system (10) includes a bioreactor (12) and a feed flow path (14). A first tangential flow filter (16) is coupled to the bioreactor (12) via the feed flow path (14) and a second tangential flow filter (18) is coupled to the bioreactor (12) via the feed flow path (14). The first tangential flow filter (16) is a microfiltration-type filter and the second tangential flow filter (18) is an ultrafiltration-type filter. The first tangential flow filter (16) and the second
(Continued)

tangential flow filter (18) are further coupled to a receiving unit (58) via the permeate flow path (60). The first tangential flow filter (16) and the second tangential flow filter (18) are further coupled to the bioreactor (12) via the retentate flow path (46). A control unit (82) is communicatively coupled to the first feed control device (42), the second feed control device (44), the feed drive unit (40), the first permeate control device (64), the second permeate control device (66), the first retentate control device (48), and the second retentate control device (50).

20 Claims, 2 Drawing Sheets

(51) Int. Cl.
*C12M 1/34* (2006.01)
*C12M 1/36* (2006.01)

(52) U.S. Cl.
CPC ............ *C12M 41/40* (2013.01); *C12M 41/48* (2013.01); *C12M 47/10* (2013.01)

(56) References Cited

U.S. PATENT DOCUMENTS

| | | | |
|---|---|---|---|
| 2016/0312168 A1 | 10/2016 | Pizzi | |
| 2019/0169559 A1 | 6/2019 | Coffman et al. | |
| 2019/0322975 A1* | 10/2019 | Nakai | C12M 29/04 |
| 2020/0181554 A1 | 6/2020 | Grant | |
| 2021/0170336 A1* | 6/2021 | Goodrich | B01D 65/02 |

OTHER PUBLICATIONS

U.S. Office Action for corresponding U.S. Appl. No. 17/782,591, mailed May 28, 2025, 14 pages.
U.S. Office Action for corresponding U.S. Appl. No. 17/782,591 mailed Jan. 13, 2026, 10 pages.

\* cited by examiner

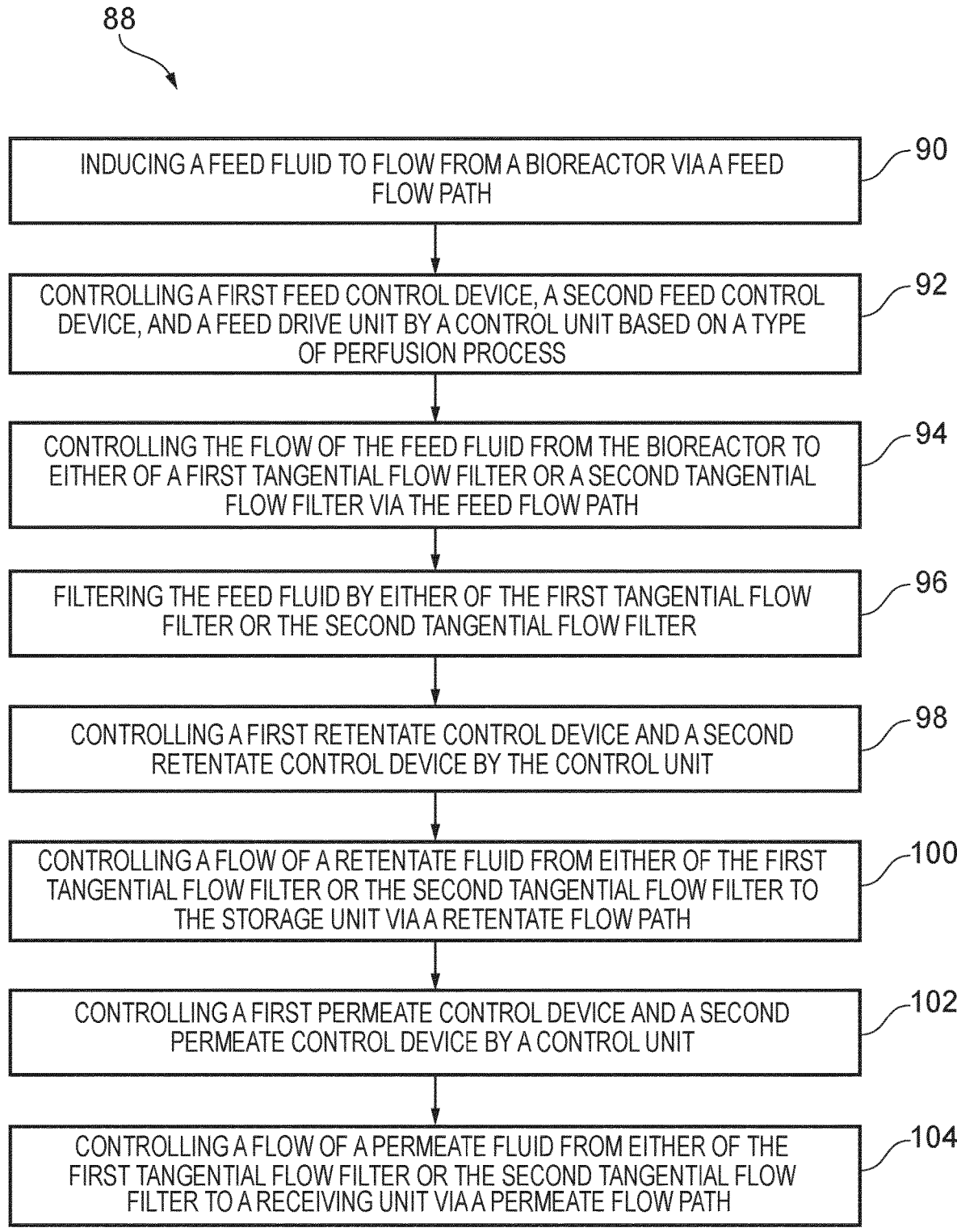

88

INDUCING A FEED FLUID TO FLOW FROM A BIOREACTOR VIA A FEED FLOW PATH — 90

CONTROLLING A FIRST FEED CONTROL DEVICE, A SECOND FEED CONTROL DEVICE, AND A FEED DRIVE UNIT BY A CONTROL UNIT BASED ON A TYPE OF PERFUSION PROCESS — 92

CONTROLLING THE FLOW OF THE FEED FLUID FROM THE BIOREACTOR TO EITHER OF A FIRST TANGENTIAL FLOW FILTER OR A SECOND TANGENTIAL FLOW FILTER VIA THE FEED FLOW PATH — 94

FILTERING THE FEED FLUID BY EITHER OF THE FIRST TANGENTIAL FLOW FILTER OR THE SECOND TANGENTIAL FLOW FILTER — 96

CONTROLLING A FIRST RETENTATE CONTROL DEVICE AND A SECOND RETENTATE CONTROL DEVICE BY THE CONTROL UNIT — 98

CONTROLLING A FLOW OF A RETENTATE FLUID FROM EITHER OF THE FIRST TANGENTIAL FLOW FILTER OR THE SECOND TANGENTIAL FLOW FILTER TO THE STORAGE UNIT VIA A RETENTATE FLOW PATH — 100

CONTROLLING A FIRST PERMEATE CONTROL DEVICE AND A SECOND PERMEATE CONTROL DEVICE BY A CONTROL UNIT — 102

CONTROLLING A FLOW OF A PERMEATE FLUID FROM EITHER OF THE FIRST TANGENTIAL FLOW FILTER OR THE SECOND TANGENTIAL FLOW FILTER TO A RECEIVING UNIT VIA A PERMEATE FLOW PATH — 104

FIG. 2

BIOPROCESSING PERFUSION SYSTEM HAVING A PLURALITY OF FILTERS AND METHOD OF OPERATING THE SAME

CROSS REFERENCE TO RELATED APPLICATIONS

This application claims the priority benefit of PCT/EP2021/069517 filed Jul. 13, 2021, which claims the priority benefit to IN application No. 202041030186 filed Jul. 15, 2020, the entire contents of which are incorporated herein by reference.

FIELD OF INVENTION

The embodiments of the present specification relate generally to bioprocessing systems, and more particularly, to a bioprocessing perfusion system having a plurality of tangential flow filters and a method for operating such a bioprocessing perfusion system.

BACKGROUND OF INVENTION

A vast array of biopharma businesses depends on filtration technology for filtration of fluids. Filtration systems are vital in food and beverage industries, chemical processing, paper and refining industries, and bioprocessing applications. Among other things, fluid filtering processing is used to accomplish one or more of the following, such as, for example, water purification, concentration, purification of a product solution or a suspension, and removal of contaminants (sterilization). Fine filtration of fluids typically involves use of membrane technology for filtration purpose.

Specifically, with reference to bioprocessing applications, cell culture has generated considerable interest in recent years due to the revolution in genetic engineering and biotechnology. Cells are cultured to make, for example, proteins, vaccines, and antibodies for therapy, research, and diagnostics.

It has long been recognized that perfusion culture offers relatively good economics for cell cultures. In such an operation, cells are retained in a bioreactor, while product is continuously removed along with toxic metabolic by-products. Feed stream (e.g., culture media), including nutrients, is added continually to the bioreactor. Perfusion culture operation can achieve high cell densities, and allows cells to be maintained in a highly productive state for longer periods. Perfusion thus achieves much higher yields and reduces the required bioreactor size. Perfusion process is also a useful technique for cultivating primary or other slow-growing cells. Perfusion process further involves fine filtration of a fluid from a bioreactor using membrane technology for harvesting cells.

As noted herein, perfusion process enables steady state continuous operation of bioreactors, for example. Applications associated with perfusion process include cell concentration, product concentration, cell/product concentration, and clarification. Typically, perfusion is performed using techniques, such as alternating tangential flow filtration, tangential flow filtration, continuous centrifugal filtration, spin filtration, or the like.

A drawback associated with use of conventional filter separation systems is that a user can perform only one process at a time, for example, cell concertation or product concentration, but not in a combined manner where, for example, cell concentration is followed by product concertation or vice versa. Additionally, at the end of a perfusion process, if a user wants to perform a clarification process to further purify or isolate the product of interest, then the user needs to connect one or more devices or replace the filter to continue the process.

A replacement of a new filter or other devices to carry out different perfusion processes currently requires manual intervention, which is disadvantageous due to concerns with sterility and process integrity, and is a time consuming process. Further, in the case of damage/wear/tear of a portion of a flow path of a conventional system, it is very difficult to perform the repair/replacement process without affecting content in the bioreactor.

There is a need for an enhanced bioprocessing perfusion system and a method for operating the bioprocessing perfusion system.

BRIEF DESCRIPTION OF INVENTION

In accordance with one embodiment, a bioprocessing perfusion system is disclosed. The bioprocessing perfusion system includes a bioreactor and a feed flow path provided with a first feed control device, a second feed control device, and a feed drive unit. The bioprocessing perfusion system further includes a first tangential flow filter coupled to the bioreactor via the feed flow path and a second tangential flow filter coupled to the bioreactor via the feed flow path. The first tangential flow filter is a microfiltration-type filter and the second tangential flow filter is an ultrafiltration-type filter. The bioprocessing perfusion system also includes a permeate flow path provided with a first permeate control device and a second permeate control device and a retentate flow path provided with a first retentate control device and a second retentate control device. The first tangential flow filter and the second tangential flow filter are further coupled to a receiving unit via the permeate flow path. The first tangential flow filter and the second tangential flow filter are further coupled to the bioreactor via the retentate flow path. Further, the bioprocessing perfusion system includes a control unit communicatively coupled to the first feed control device, the second feed control device, the feed drive unit, the first permeate control device, the second permeate control device, the first retentate control device, and the second retentate control device. The control unit is configured to control the first feed control device, the second feed control device, the feed drive unit, the first retentate control device, the second retentate control device, the first permeate control device, and the second permeate control device. The control steps enables controlling a flow of a feed fluid from the bioreactor to either of the first tangential flow filter or the second tangential flow filter via the feed flow path, a flow of a retentate fluid from either of the first tangential flow filter or the second tangential flow filter to the bioreactor via the retentate flow path, and a flow of a permeate fluid from either of the first tangential flow filter or the second tangential flow filter to the receiving unit via the permeate flow path, based on a type of a perfusion process.

In accordance with another embodiment, a method for operating a bioprocessing perfusion system is disclosed. The method includes inducing a feed fluid to flow from a bioreactor via a feed flow path. The method further includes controlling, by a control unit, a first feed control device, a second feed control device, a feed drive unit, a first retentate control device, a second retentate control device, a first permeate control device, and a second permeate control device. The control step includes controlling a flow of the feed fluid from the bioreactor to either of a first tangential flow filter or a second tangential flow filter via the feed flow path, a flow of a retentate fluid from either of the first tangential flow filter or the second tangential flow filter to the bioreactor via a retentate flow path, and/or a flow of a permeate fluid from either of the first tangential flow filter or the second tangential flow filter to a receiving unit via the permeate flow path, based on a type of a perfusion process.

BRIEF DESCRIPTION OF DRAWINGS

These and other features, aspects, and advantages of the present disclosure will become better understood when the following detailed description is read with reference to the accompanying drawings in which like characters represent like parts throughout the drawings, wherein:

FIG. 2 is a flow chart illustrating a plurality of steps involved in a method for operating the bioprocessing perfusion system having the plurality of tangential flow filters, in accordance with an embodiment of the present specification.

DETAILED DESCRIPTION

Figure 1:
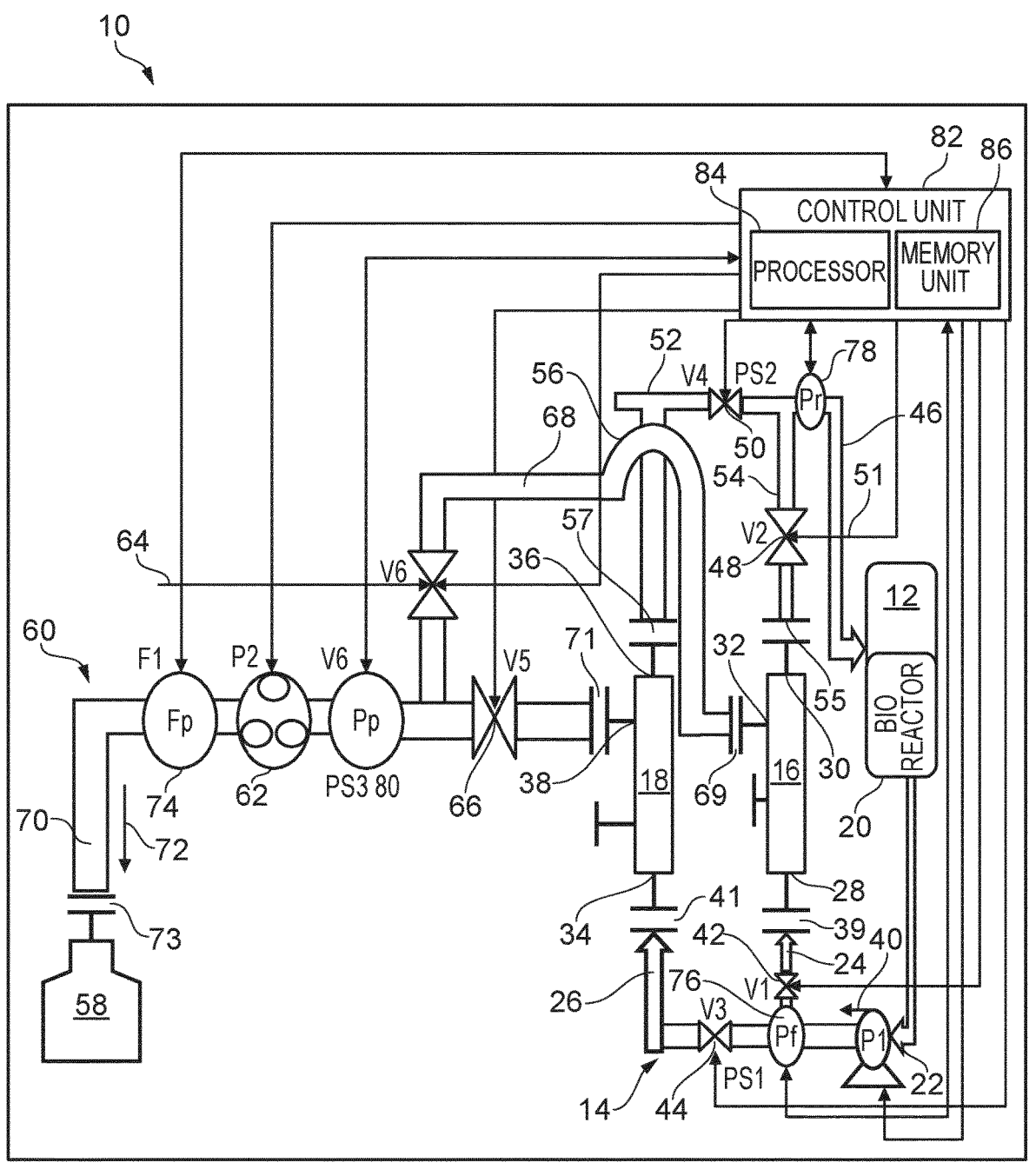
FIG. 1 is a schematic diagram of a bioprocessing perfusion system having a plurality of tangential flow filters in accordance with an embodiment of the present specification.

For the purpose of promoting an understanding of the principles of the disclosure, reference will now be made to an embodiment illustrated in the figures and specific language will be used to describe them. It will nevertheless be understood that no limitation of the scope of the disclosure is thereby intended. Such alterations and further modifications to the disclosure, and such further applications of the principles of the disclosure as described herein being contemplated as would normally occur to one skilled in the art to which the disclosure relates are deemed to be a part of this disclosure.

It will be understood by those skilled in the art that the foregoing general description and the following detailed description are exemplary and explanatory of the disclosure and are not intended to be restrictive thereof.

Unless defined otherwise, technical and scientific terms used herein have the same meaning as is commonly understood by one of ordinary skill in the art to which this disclosure belongs. The terms "first," "second," and the like, as used herein do not denote any order, quantity, or importance, but rather are used to distinguish one element from another. The terms "comprises", "comprising", or any other variations thereof, are intended to cover a non-exclusive inclusion, such that a process or method that comprises a list of steps does not include only those steps but may include other steps not expressly listed or inherent to such a process or a method. Similarly, one or more devices or sub-systems or elements or structures or components preceded by "comprises . . . a" does not, without more constraints, preclude the existence of other devices, other sub-systems, other elements, other structures, other components, additional devices, additional sub-systems, additional elements, additional structures, or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this disclosure belongs. The system, methods, and examples provided herein are illustrative only and not intended to be limiting.

Embodiments of the present disclosure will be described below in detail with reference to the accompanying figures.

In accordance with one embodiment of the present disclosure, a bioprocessing perfusion system is disclosed. The bioprocessing system includes a bioreactor and a feed flow path provided with a first feed control device, a second feed control device, and a feed drive unit. The bioprocessing system also includes a first tangential flow filter and a second tangential flow filter coupled to the bioreactor via the feed flow path. The first tangential flow filter is a microfiltration-type filter. The second tangential flow filter is an ultrafiltration-type filter. Further, the bioprocessing system includes a permeate flow path provided with a first permeate control device and a second permeate control device and a retentate flow path provided with a first retentate control device and a second retentate control device. The first tangential flow filter and the second tangential flow filter are further coupled to a receiving unit via the permeate flow path. The first tangential flow filter and the second tangential flow filter are further coupled to the bioreactor via the retentate flow path. Furthermore, the bioprocessing perfusion system includes a control unit communicatively coupled to the first feed control device, the second feed control device, the feed drive unit, the first permeate control device, the second permeate control device, the first retentate control device, and the second retentate control device. The control unit is configured to control the first feed control device, the second feed control device, the feed drive unit, the first retentate control device, the second retentate control device, the first permeate control device, and the second permeate control device for controlling a flow of a feed fluid from the bioreactor to either of the first tangential flow filter or the second tangential flow filter via the feed flow path, a flow of a retentate fluid from either of the first tangential flow filter or the second tangential flow filter to the bioreactor via the retentate flow path, and a flow of a permeate fluid from either of the first tangential flow filter or the second tangential flow filter to the receiving unit via the permeate flow path, based on a type of a perfusion process.

In accordance with another embodiment, a method for operating the bioprocessing perfusion system is disclosed. The exemplary system and method enable use of filters based on the intended perfusion application. The exemplary system and method facilitate performing different perfusion applications without stoppage of the process or changeover of filters or change of process parameters.

Referring to FIG. 1, a schematic diagram of a bioprocessing perfusion system 10 in accordance with an embodiment of the present specification is shown. In the illustrated embodiment, the bioprocessing perfusion system 10 includes a bioreactor 12 coupled via a feed flow path 14 to a first tangential flow filter 16 and a second tangential flow filter 18. In one embodiment, the bioreactor 12 is used to store a feed fluid 20, for example, a cell culture medium along with cells that are being cultivated. In one embodiment, the first and second tangential flow filters 16, 18 may be hollow fiber filters. In another embodiment, the first and second tangential flow filters 16, 18 may be cassette filters. The feed flow path 14 has a main feed portion 22 and first and second branch feed portions 24, 26 extending from the main portion 22. In the illustrated embodiment, the first and second branch feed portions 24, 26 extend parallel to each other, but other configurations are contemplated. The first tangential flow filter 16 has an inlet 28, a first outlet 30, and a second outlet 32. The second tangential flow filter 18 has an inlet 34, a first outlet 36, and a second outlet 38. Specifically, the first branch feed portion 24 is coupled to the inlet 28 of the first tangential flow filter 16 via a first outlet aseptic feed connector 39. The second branch feed portion 26 is coupled to the inlet 34 of the second tangential flow filter 18 via a second outlet aseptic feed connector 41. The main feed portion 22 may be connected to the bioreactor 12 via a similar inlet aseptic feed connector (not shown). In one embodiment, the first tangential flow filter 16 is a microfiltration-type filter and the second tangential flow filter 18 is an ultrafiltration-type filter. As noted herein, the terms "first," "second," and the like, as used herein do not denote any order, quantity, or importance, but rather are used to distinguish one element from another.

The bioprocessing system 10 further includes a feed drive unit 40 (for example, feed pump), a first feed control device 42, and a second feed control device 44 coupled to the feed flow path 14. In one embodiment, the feed first control device 42 and the second feed control device 44 may also be referred to herein as a feed control valve. Specifically, the first feed control device 42 is disposed downstream of the feed drive unit 40 and upstream of the first tangential flow filter 16. More specifically, the first feed control device 42 is coupled to the first branch feed portion 24 and the second feed control device 44 is coupled to the main feed portion 22. The second feed control device 44 is located downstream of the first branch feed portion 24 and upstream of the second branch feed portion 26. In another embodiment, the second feed control device 44 is coupled to the second branch feed portion 26. Further, the feed drive unit 40 is used for feeding the feed fluid 20 at a predetermined flow rate from the bioreactor 12 to the first tangential flow filter 16 or the second tangential flow filter 18 via the feed flow path 14. The first feed control device 42 and the second feed control device 44 are used for controlling a flow of the feed fluid 20 via the feed flow path 14 to the first tangential flow filter 16 or the second tangential flow filter 18.

Further, the bioreactor 12 is coupled to the first outlet 30 of the first tangential flow filter 16 and the first outlet 36 of the second tangential flow filter 18 via a retentate flow path 46. A first retentate control device 48 and a second retentate control device 50 are coupled to the retentate flow path 46. Specifically, the first and second retentate control devices 48, 50 are used to control a flow of a retentate fluid 51 through the retentate flow path 46 to the bioreactor 12. The first retentate control device 48 and the second retentate control device 50 may also be referred to herein as a "retentate control valve". The retentate flow path 46 has a main retentate portion 52 and first and second branch retentate portions 54, 56 extending from the main retentate portion 52. In the illustrated embodiment, the first and second branch retentate portions 54 56 extend parallel to each other, but other configurations are contemplated. Specifically, the first retentate control device 48 is coupled to the first branch retentate portion 54 and the second retentate control device 50 is coupled to the main retentate portion 52. The second retentate control device 50 is located upstream of the first branch retentate portion 54 and downstream of the second branch retentate portion 56. Specifically, the first and second branch retentate portions 54, 56 are coupled respectively to first outlet 30 of the first tangential flow filter 16 and the first outlet 36 of the second tangential flow filter 18 via respective first and second inlet aseptic retentate connectors 55, 57. In another embodiment, the second retentate control device 50 is coupled to the second branch retentate portion 56. The main retentate portion 52 may also be coupled to the bioreactor via an outlet aseptic retentate connector (not shown). The first tangential flow filter 16 or the second tangential flow filter 18 are used for separating the retentate fluid 51 from the feed fluid 20 by utilizing a pressure difference across the first and second tangential flow filters 16, 18.

Additionally, a receiving unit 58 is coupled to the second outlets 32, 38 of the first and second tangential flow filters 16, 18 via a permeate flow path 60. The bioprocessing system 10 also includes a permeate pump 62 coupled to the permeate flow path 60. Also, the bioprocessing system 10 includes a first permeate control device 64 and a second permeate control device 66 coupled to the permeate flow path 60 and disposed upstream of the permeate pump 62. The first and second permeate control devices 64, 66 may also be referred to herein as a "permeate control valve". The permeate flow path 60 has a first permeate flow path portion 68 and a second permeate flow path portion 70. Specifically, the first permeate control device 64 is coupled to the first permeate flow path portion 68 and the second permeate control device 66 is coupled to the second permeate flow path portion 70. The first tangential flow filter 16 is coupled to the receiving unit 58 via the first permeate flow path portion 68 and the second permeate flow path portion 70. Specifically, the first permeate flow path portion 68 and the second permeate flow path portion 70 are coupled respectively to the second outlets 32, 38 of the first and second tangential flow filters 16, 18 via respective first and second inlet aseptic permeate connectors 69, 71. The second tangential flow filter 18 is coupled to the receiving unit 58 via the second permeate flow path portion 70. Specifically, the first permeate flow path portion 68 is coupled to the second permeate flow path portion 70 at a location downstream of the second permeate control device 66. The second permeate control device 66 is located upstream of the first permeate flow portion 70. The second permeate flow path portion 70 is coupled to the receiving unit 58 via an outlet aseptic permeate connectors 73.

The first or second tangential flow filters 16, 18 are used for separating a permeate fluid 72 from the feed fluid 20 by utilizing a transmembrane pressure across the first and second tangential flow filters 16, 18. The permeate pump 62 can be operated to feed the permeate fluid 72 at a predetermined flow rate to the receiving unit 58 via the permeate flow path 60. The first and second permeate control devices 64, 66 are used to control the flow of the permeate fluid 72 via the permeate flow path 60 to the receiving unit 58.

In the illustrated embodiment, the bioprocessing system 10 further includes a permeate flow sensor 74 coupled to the permeate flow path 60. Specifically, the permeate flow sensor 74 is disposed downstream of the first and second permeate control devices 64, 66 and the permeate pump 62. The permeate flow sensor 74 is used to measure a flow rate of the permeate fluid 72 flowing through the permeate flow path 60. In one embodiment, the permeate flow sensor 74 may output a signal representative of the flow rate of the permeate fluid 72 flowing through the permeate flow path 60. In another embodiment, the permeate flow sensor 74 may output a signal representative of a parameter, for example, volume or velocity, of the permeate fluid 72 for computing the flow rate of the permeate fluid 72. Any type of flow sensor which may be used for measuring the flow rate of the permeate fluid 72 is envisioned.

It should be noted herein that the illustrated bioprocessing system 10 is an exemplary embodiment and should not be construed as a limitation. The configuration of the bioprocessing system 10 may vary depending upon the application.

In other embodiments, the number and positions of filters, control devices, and sensors may vary depending on the application and process requirements.

In another embodiment, instead of a feed pump, a pressurized gas may be fed from a gas source (not shown) to the bioreactor 12 via a filter (not shown) for feeding the feed fluid 20 from the bioreactor 12 to the first or second tangential flow filters 16, 18 via the feed flow path 14.

As discussed earlier, a drawback associated with use of conventional filter separation systems is that a user can perform only one process at a time, for example, cell concertation or product concentration, but not in a combined manner where for example, cell concentration is followed by product concertation or vice versa. Additionally, at the end of a perfusion process, if a user wants to perform a clarification process to further purify or isolate the product of interest, the user needs to connect one more devices or replace the filter to continue the process. A replacement of a filter or other device(s) to carry out perfusion thus requires manual intervention which is disadvantageous due to concerns with sterility and process integrity, and is a time consuming process.

In the illustrated embodiment, the bioprocessing system 10 further includes a feed pressure sensor 76 coupled to the feed flow path 14. Specifically, the feed pressure sensor 76 is coupled to the main feed portion 22 of the feed flow path 14. The feed pressure sensor 76 is located downstream of the feed drive unit 40 and upstream of the first and second branch feed portions 24, 26. The feed pressure sensor 76 is used to sense a pressure of the feed fluid 20 flowing through the main feed portion 22 of the feed flow path 14. Additionally, a retentate pressure sensor 78 is coupled to the main retentate portion 52 of the retentate flow path 46. Specifically, the retentate pressure sensor 78 is disposed downstream of the first and second branch retentate portions 54, 56 of the retentate flow path 46. The retentate pressure sensor 78 is used to sense a pressure of the retentate fluid 51 flowing through the main retentate portion 52 of the retentate flow path 46.

Additionally, a permeate pressure sensor 80 is coupled to the second permeate flow path portion 70. The permeate pressure sensor 80 is located upstream of the permeate pump 62 and downstream of the location at which the first permeate flow path portion 68 is connected to the second permeate flow path portion 70. The permeate pressure sensor 80 is used to sense a pressure of the permeate fluid 72 flowing through the second permeate flow path portion 70. In the illustrated embodiment, a transfer pump (not shown) may be used in washing and diafiltration applications to add a liquid (usually buffer) from a source unit (not shown) to the bioreactor 12 at a predefined controlled rate.

Further, in the illustrated embodiment, the bioprocessing system 10 includes a control unit 82 having a processor 84 and a memory unit 86 coupled to the processor 84. In some embodiments, the control unit 82 is used to control at least one function of the bioprocessing system 10. In certain embodiments, the control unit 82 may include more than one processor co-operatively working with each other for performing intended functionalities. The control unit 82 is further configured to store and retrieve contents into and from the memory unit 86.

In one embodiment, the processor 84 includes at least one of a general-purpose computer, a graphics processing unit (GPU), a digital signal processor, and a controller. In some embodiments, the processor 84 may be implemented as one or more microprocessors, microcomputers, microcontrollers, digital signal processors, central processing units, state machines, logic circuitries, and/or any device that manipulates signals based on operational instructions. Among other capabilities, the at least one processor is configured to fetch and execute computer-readable instructions stored in the memory. In other embodiments, the processor 84 includes a customized processor element such as, but not limited to, an application-specific integrated circuit (ASIC) and a field-programmable gate array (FPGA). In some embodiments, the processor 84 may be communicatively coupled with at least one of a keyboard, a mouse, and any other input device and configured to receive commands and/or parameters from an operator via a console.

In one embodiment, the memory unit 86 is a random-access memory (RAM), a read only memory (ROM), a flash memory, or any other type of computer readable memory accessible by the processor 84. In some embodiments, the memory unit 86 may include, for example, volatile memory such as static random access memory (SRAM) and/or dynamic random access memory (DRAM) and/or non-volatile memory such as read only memory (ROM), erasable programmable ROM, flash memories, hard disks, optical disks, and/or magnetic tapes. Also, in certain embodiments, the memory unit 86 may be a non-transitory computer readable medium encoded with a program having a plurality of instructions to instruct the processor 84 to perform a sequence of steps to operate bioprocessing system 10.

In certain embodiments, the control unit 82 may include an I/O interface having a variety of client application and hardware interfaces, for example, a web interface, a graphical user interface, and the like. The I/O interface may allow the control unit 82 to interact with a customer directly or through customer devices. Further, the I/O interface may enable the control unit 82 to communicate with other computing devices such as web servers and external data servers (not shown). The I/O interface may facilitate multiple communications within a wide variety of networks and protocol types, including wired networks such as Local Area Network, cable, etc., and wireless networks such as Wireless Local Area Network, cellular, satellite, etc. The I/O interface may include one or more ports for connecting a plurality of devices to each other and/or to another server.

In some embodiments, the control unit 82 can also be communicatively coupled to the feed drive unit 40 and the permeate pump 62. The control unit 82 is further configured to control the feed drive unit 40 and the permeate pump 62. Furthermore, the control unit 82 can also be coupled to and configured to control operations of the first feed control device 42, the second feed control device 44, the first and second permeate control devices 64, 66, and the first and second retentate control devices 48, 50.

The control unit 82 is configured to control the first feed control device 42, the second feed control device 44, the feed drive unit 40, in order to control a flow of the feed fluid 20 from the bioreactor 12 to either of the first tangential flow filter 16 or the second tangential flow filter 18 via the feed flow path 14. The control unit 82 is also configured to control the first retentate control device 48 and the second retentate control device 50 in order to control the flow of the retentate fluid 51 from either of the first tangential flow filter 16 or the second tangential flow filter 18 to the bioreactor 12 via the retentate flow path 46. The control unit 82 is still further configured to control the first permeate control device 64 and the second permeate control device 66 in order to control a flow of the permeate fluid 72 from either of the first tangential flow filter 16 or the second tangential flow filter 18 to the receiving unit 58 via the permeate flow path 60, based on a type of a perfusion process. The type of the perfusion process is one among, but not limited to, a cell retention process, a product and cell retention process, a clarification process, and a product concentration process.

In the illustrated embodiment, the control unit 82 is communicatively coupled to the permeate flow sensor 74. In one embodiment, the control unit 82 is configured to receive an output signal representative of the flow rate of the permeate fluid 72 from the permeate flow sensor 74. In another embodiment, the control unit 82 is configured to receive an output signal representative of a parameter, for example, volume or velocity, of the permeate fluid 72 from the permeate flow sensor 74 to compute the flow rate of the permeate fluid 72. In one embodiment, the control unit 82 determines a permeate flux rate of the first tangential flow filter 16 or the second tangential flow filter 18 based on the determined flow rate of the permeate fluid 72 by the permeate flow sensor 74. It should be noted herein that the permeate flux rate of the first tangential flow filter 16 or the second tangential flow filter 18 is defined as the measured flow rate of the permeate fluid 72 per unit area of the first tangential flow filter 16 or the second tangential flow filter 18. The control unit 82 is configured to operate the bioprocessing perfusion system 10 in a flux control mode based on the determined permeate flux rate. In the flux control mode, the flux is maintained at a controlled rate by regulating flow of the feed fluid 20 or the retentate fluid 51 and the permeate fluid 72. It should be noted herein that flux control mode is used for a microfiltration process where the bioprocessing system limits the flow of the permeate fluid 72 through the relatively large pores of the filter membrane.

Additionally, the control unit 82 is communicatively coupled to the feed pressure sensor 76, the retentate pressure sensor 78, and the permeate pressure sensor 80. In one embodiment, the control unit 82 is communicatively coupled to the feed, retentate, and permeate pressure sensors 76, 78, 80 and configured to determine a Trans-Membrane Pressure (TMP) of the first tangential flow filter 16 or the second tangential flow filter 18 based on outputs from the feed, retentate, and permeate pressure sensors 76, 78, 80. It should be noted herein that the TMP is representative of a pressure that is needed to pass a fluid medium through a filter. The control unit 82 is configured to determine an operating condition, for example, clogged condition of the first tangential flow filter 16 or the second tangential flow filter 18 based on the determined transmembrane pressure. In another embodiment, the control unit 82 is configured to determine a pressure difference across the first tangential flow filter 16 or the second tangential flow filter 18 based outputs from the feed and retentate pressure sensors 76, 78.

FIG. 2 is a flow chart illustrating a method 88 for operating the bioprocessing system 10 in accordance with the embodiment of FIG. 1. The method 88 includes inducing the flow of the feed fluid 20 from the bioreactor 12 via the feed flow path 14 as represented by step 90. The control unit 82 operates the feed drive unit 40, the first feed flow control devices 42, and the second feed flow control device 44 to control the flow of the feed fluid 20 from the bioreactor 12 via the feed flow path 14 based on a type of perfusion process as represented by step 92. The type of the perfusion process is one among, but not limited to, a cell retention process, a product and cell retention process, a clarification process, and a product concentration process. The method 88 includes controlling the flow of the feed fluid 20 from the bioreactor 12 to either of the first tangential flow filter 16 or the second tangential flow filter 18 via the feed flow path 14 as represented by step 94. In one embodiment, the first tangential flow filter 16 is a microfiltration-type filter and the second tangential flow filter 18 is an ultrafiltration-type filter. In one embodiment, the first tangential flow filter 16 has pore sizes which is greater than or equal to 0.1 μm, for example. In some embodiments, the pore size of the first tangential flow filter 16 is usually in the range 0.1 to 1 μm. In one embodiment, the second tangential flow filter 18 has pore sizes in a range 20 to 100 nm, for example, and are generally characterized in terms of the nominal molecular weight cutoff (NMWC), which is a molecular weight of largest globular protein that can pass through a filter membrane. The NMWC values may range from 1 to 100 kD (kiloDalton). The objective of most ultrafiltration processes is to retain soluble macromolecules such as proteins above a certain size, while allowing smaller molecules such as salts, amino acids, and mono- or disaccharides to pass through the filter membrane.

If the first feed flow control device 42 is opened and the second feed flow control device 44 is closed, the feed fluid 42 is routed through the first tangential flow filter 16. If the first feed flow control device 42 is closed and the second feed flow control device 44 is opened, the feed fluid 20 is routed through the second tangential flow filter 18.

In one embodiment, the method 88 includes directing the flow of the feed fluid 20 from the bioreactor 12 to the first tangential flow filter 16 via the feed flow path 14 if the type of the perfusion process is a cell retention process (i.e. microfiltration). In another embodiment, the method 88 includes directing the flow of the feed fluid 20 from the bioreactor 12 to the second tangential flow filter 18 via the feed flow path 14 if the type of the perfusion process is a product and cell retention process (i.e. ultrafiltration). In yet another embodiment, the method 88 incudes directing the flow of the feed fluid 20 from the bioreactor 12 to the first tangential flow filter 16 via the feed flow path 14 if the type of the perfusion process is a clarification process (i.e. microfiltration). In yet another embodiment, the method 88 includes directing the flow of the feed fluid 20 from the bioreactor 12 to the second tangential flow filter 18 via the feed flow path 14 if the type of the perfusion process is the product concentration process (i.e. ultrafiltration).

Cell harvesting/retention involves separation of cells from soluble molecules of the feed fluid 20, for example, fermentation broth and then recovering the cells in the retentate fluid 51. Cell or lysate clarification involves separation of target molecules from intact cells, cell debris and molecular aggregates from soluble molecules and then recovering the target molecules in the permeate fluid 72. Specifically, cell clarification is used to recover a target protein that is expressed in the culture medium during cell culture. The cells are filtered and remain in the feed/retentate flow path, while the permeate fluid 72 includes the protein or molecule of interest. Also, lysate clarification is used after lysis of harvested cells to recover the target molecule from the cell contents. Product concentration of the feed fluid 20 involves removal of solvent and small molecules and then recovering the product in the retentate fluid 51. In other words, the product concentration involves separating macromolecules from low molecular weight buffer components.

It should be noted herein that filter selectivity defines the ability of a filter to separate particles or molecular species based on size. A filter with a narrow pore size distribution will be highly selective, while a broader pore size distribution would provide a less selective filter. For example, cell harvesting and cell clarification applications involve separation of relatively large particles (cells and/or cell debris) from macromolecules. Hence, high selectivity filter is generally not required. Lysate clarification may require more stringent demands, since the lysate includes a wide range of proteins and other macromolecules. The most important factor is that the target protein can pass freely through the filter so that yields are not compromised.

The method 88 further includes filtering the feed fluid 20 by either of the first tangential flow filter 16 or the second tangential flow filter 18 as represented by step 96. The first tangential flow filter 16 or the second tangential filter separates the feed fluid 20 into the permeate fluid 72 and the retentate fluid 51. Specifically, the feed fluid 20 is passed tangentially across the first tangential flow filter 16 or the second tangential flow filter 18 at positive pressure relative to a permeate side of the first tangential flow filter 16 or the second tangential flow filter 18. Further, the method 88 includes controlling the first retentate control device 48 and the second retentate control device 50 by the control unit 82 as represented by the step 98. The method 88 further includes controlling a flow of the retentate fluid 51 from either of the first tangential flow filter 16 or the second tangential flow filter 18 to the bioreactor 12 via the retentate flow path 46 as represented by the step 100. If the first retentate flow control device 48 is opened and the second retentate flow control device 50 is closed, the retentate fluid 51 flows from the first tangential flow filter 16 to the bioreactor 12 via the retentate flow path 46. If the first retentate flow control device 48 is closed and the second retentate flow control device 50 is opened, the retentate fluid 51 flows from the second tangential flow filter 18 to the bioreactor 12 via the retentate flow path 46.

The method 88 further includes controlling the first permeate control device 64 and the second permeate control device 66 by the control unit 82 as represented by the step 102. The control unit 82 operates the permeate pump 62 and controls the first permeate flow control device 64 and the second permeate flow control device 66 to feed the permeate fluid 72 from either of the first tangential filter 16 or the second tangential flow filter 18 to the receiving unit 58 via the permeate flow path 60 as represented by the step 104. If the first permeate flow control device 64 is opened and the second permeate flow control device 66 is closed, the permeate fluid 72 is fed from the first tangential flow filter 16 to the receiving unit 58 via the first permeate flow path portion 68 and the second permeate flow path portion 70. If the first permeate flow control device 64 is closed and the second permeate flow control device 66 is opened, the permeate fluid 72 is fed from the second tangential filter 18 to the receiving unit 58 via the second permeate flow path portion 70.

In one embodiment, the control unit 82 determines a permeate flux rate of the first tangential flow filter 16 or the second tangential flow filter 18 based on the determined flow rate of the permeate fluid 72 by the permeate flow sensor 74. The control unit 82 is configured to operate the bioprocessing perfusion system 10 in a flux control mode based on the determined permeate flux rate.

In yet another embodiment, the control unit 82 determines the clogged condition of the first tangential flow filter 16 or the second tangential flow filter 18 based on the determined TMP of the first tangential flow filter 16 or the second tangential flow filter 18, a pressure difference between a feed fluid pressure and a retentate fluid pressure, and a permeate pressure. The TMP is computed based on outputs from the feed, retentate, and permeate pressure sensors 76, 78, 80. Specifically, according to one embodiment, the TMP is calculated by the control unit 82 based on the following relation:

$$TMP=((p2+p3)/2)-p1$$

where p1 is an output of the permeate pressure sensor 80, p2 is an output of the feed pressure sensor 76, p3 is an output of the retentate pressure sensor 78. If the TMP, or the pressure difference between the feed fluid pressure and the retentate fluid pressure, or the permeate fluid pressure is greater is greater than a threshold pressure, the control unit 82 determines clogging of the first tangential flow filter 16 or the second tangential flow filter 18.

The exemplary system and method enable perfusion process using at least two tangential flow filters. The type of tangential flow filter can be used based on the intended perfusion application, which requires either microfiltration or ultrafiltration. In one embodiment, the bioprocessing system 10 may perform both cell retention followed by clarification, by the first tangential flow filter 16. In another embodiment, the bioprocessing system 10 may perform clarification by the first tangential flow filter 16 followed by product and cell retention by the second tangential flow filter 18. In yet another embodiment, the bioprocessing system 10 may perform cell retention by the first tangential flow filter 16 and then product concentration by the second tangential flow filter 18. In yet another embodiment, the bioprocessing system 10 may perform clarification by the first tangential flow filter 16 followed by product concentration by the second tangential flow filter 18. All such permutations and combinations are envisioned. It should be noted herein sequencing of a flow of the feed fluid 20 is always from the first tangential flow filter 16 to the second tangential flow filter 18 and not vice versa depending on the application. The exemplary system and method enable a user to perform a plurality of perfusion processes in a combined manner where for example, cell concentration is followed by product concertation or vice versa. There is no need for a user to connect one or more additional devices or replace a filter to continue the process. Hence, there is no requirement of a manual intervention, thereby overcoming drawbacks associated with sterility, process integrity, and time consumption. Furthermore, the provision of aseptic connectors facilitates to isolate a corresponding complete fluid flow path so that the damaged flow path section/part can be replaced without damaging contents of the bioreactor.

While only certain features of the specification have been illustrated and described herein, many modifications and changes will occur to those skilled in the art. It is, therefore, to be understood that the appended claims are intended to cover all such modifications and changes as fall within the true spirit of the specification.

We claim:

1. A bioprocessing perfusion system comprising: a bioreactor; a feed flow path provided with a first feed control device, a second feed control device, and a feed drive unit; a first tangential flow filter coupled to the bioreactor via the feed flow path, wherein the first tangential flow filter is a microfiltration-type filter; a second tangential flow filter coupled to the bioreactor via the feed flow path, wherein the second tangential flow filter is an ultrafiltration-type filter, a permeate flow path provided with a first permeate control device and a second permeate control device, wherein the first tangential flow filter and the second tangential flow filter are further coupled to a receiving unit via the permeate flow path; a retentate flow path provided with a first retentate control device and a second retentate control device, wherein the first tangential flow filter and the second tangential flow filter are further coupled to the bioreactor via the retentate flow path; wherein a type of perfusion process is one of a cell retention process, a product and cell retention process, a clarification process, and a product concentration process; and a control unit communicatively coupled to the first feed control device, the second feed control device, the feed drive unit, the first permeate control device, the second permeate control device, the first retentate control device, and the second retentate control device, wherein the control unit is configured to control the first feed control device, the second feed control device, the feed drive unit, the first retentate control device, the second retentate control device, the first permeate control device, and the second permeate control device for: directing the flow of the feed fluid from the bioreactor to the first tangential flow filter via the feed flow path if the type of the perfusion process is the cell retention process; directing the flow of the feed fluid from the bioreactor to the second tangential flow filter via the feed flow path if the type of the perfusion process is the product and cell retention process; directing the flow of the feed fluid from the bioreactor to the first tangential flow filter via the feed flow path if the type of the perfusion process is the clarification process; and directing the flow of the feed fluid from the bioreactor to the second tangential flow filter via the feed flow path if the type of the perfusion process is the product concentration process.

2. The bioprocessing perfusion system as claimed in claim 1, further comprising a permeate flow sensor coupled to the permeate flow path, wherein the control unit is communicatively coupled to the permeate flow sensor.

3. The bioprocessing perfusion system as claimed in claim 1, further comprising:

a feed pressure sensor coupled to the feed flow path;

a retentate pressure sensor coupled to the retentate flow path; and a permeate pressure sensor coupled to the permeate flow path;

wherein the control unit is communicatively coupled to the feed, retentate, and permeate pressure sensors.

4. The bioprocessing perfusion system as claimed in claim 1, wherein the feed flow path comprises a main feed portion, a first branch feed portion, and a second branch feed portion, wherein the bioreactor is coupled to the first tangential flow filter via the main feed portion and the first branch feed portion, and wherein the bioreactor is coupled to the second tangential flow filter via the main feed portion and the second branch feed portion.

5. The bioprocessing perfusion system as claimed in claim 1, wherein the first feed control device is coupled to the first branch feed portion, wherein the second feed control device is coupled to the main feed portion or the second branched feed portion, and wherein the second feed control device is located downstream of the first branch feed portion.

6. The bioprocessing perfusion system as claimed in claim 1, wherein the permeate flow path comprises a first permeate flow path portion (and a second permeate flow path portion, wherein the first tangential flow filter is coupled to the receiving unit via the first permeate flow path portion and second permeate flow path portion.

7. The bioprocessing perfusion system as claimed in claim 6, wherein the second tangential flow filter is coupled to the receiving unit via the second permeate flow path portion.

8. The bioprocessing perfusion system as claimed in claim 6, wherein the first permeate control device is coupled to the first permeate flow path portion, wherein the second permeate control device is coupled to the second permeate flow path portion, and wherein the first permeate flow path portion is coupled to the second permeate flow path portion at a location downstream of the second permeate control device.

9. The bioprocessing perfusion system as claimed in claim 1, wherein the retentate flow path comprises a main retentate portion, a first branch retentate portion, and a second branch retentate portion, wherein the bioreactor is coupled to the first tangential flow filter via the main retentate portion and the first branch retentate portion, and wherein the bioreactor is coupled to the second tangential flow filter via the main retentate portion and the second branch retentate portion.

10. The bioprocessing perfusion system as claimed in claim 9, wherein the first retentate control device is coupled to the first branch retentate portion, wherein the second retentate control device is coupled to the main retentate portion or the second branched retentate portion, and wherein the second retentate control device is located upstream of the first branch retentate portion.

11. The bioprocessing perfusion system as claimed in claim 1, wherein each of the feed flow path, the permeate flow path, and the retentate flow path is provided with an inlet aseptic connector and an outlet aseptic connector.

12. The bioprocessing perfusion system as claimed in claim 1, wherein the type of the perfusion process is one of a cell retention process, a product and cell retention process, a clarification process, and a product concentration process.

13. A method for operating a bioprocessing perfusion system, the method comprising:

inducing a feed fluid to flow from a bioreactor via a feed flow path; and controlling, by a control unit, a first feed control device, a second feed control device, a feed drive unit, a first retentate control device, a second retentate control device, a first permeate control device, and a second permeate control device to control a flow of the feed fluid from the bioreactor to either of a first tangential flow filter or a second tangential flow filter via the feed flow path, a flow of a retentate fluid from either of the first tangential flow filter or the second tangential flow filter to the bioreactor via a retentate flow path, and/or a flow of a permeate fluid from either of the first tangential flow filter or the second tangential flow filter to a receiving unit via the permeate flow path, based on a type of a perfusion process, wherein the feed flow path is provided with the first feed control device, the second feed control device, and the feed drive unit, wherein the permeate flow path is provided with the first permeate control device and the second permeate control device, wherein the retentate flow path is provided with the first retentate control device and the second retentate control device, wherein the first tangential flow filter is a microfiltration type-filter, wherein the second tangential flow filter is an ultrafiltration type filter, and wherein the type of the perfusion process is one of a cell retention process, a product and cell retention process, a clarification process, and a product concentration process.

14. The method as claimed in claim 13, further comprising determining a flow rate of the permeate fluid in the permeate flow path by a permeate flow sensor.

15. The method as claimed in claim 14, further comprising:

determining, by the control unit, a permeate flux rate of the first tangential flow filter or the second tangential flow filter based on the determined flow rate of the permeate fluid; and operating, by the control unit, the bioprocessing perfusion system in a flux control mode based on the determined permeate flux rate.

16. The method as claimed in claim 13, further comprising determining, by the control unit, a pressure of the feed fluid by a feed pressure sensor;

determining, by the control unit, a pressure of the retentate fluid by a retentate pressure sensor; and determining, by the control unit, a pressure of the permeate fluid by a permeate pressure sensor; and determining, by the control unit, a transmembrane pressure (TMP) based on the pressure of the feed fluid, the pressure of the retentate fluid, and the pressure of the permeate fluid; and determining, by the control unit, an operating condition of the first tangential flow filter or the second tangential flow filter based on the determined transmembrane pressure.

17. The method as claimed in claim 13, further comprising directing the flow of the feed fluid from the bioreactor to the first tangential flow filter via the feed flow path if the type of the perfusion process is the cell retention process.

18. The method as claimed in claim 13, further comprising directing the flow of the feed fluid from the bioreactor to the second tangential flow filter via the feed flow path if the type of the perfusion process is the product and cell retention process.

19. The method as claimed in claim 13, further comprising directing the flow of the feed fluid from the bioreactor to the first tangential flow filter via the feed flow path if the type of the perfusion process is the clarification process.

20. The method as claimed in claim 13, further comprising directing the flow of the feed fluid from the bioreactor to the second tangential flow filter via the feed flow path if the type of the perfusion process is the product concentration process.

\*   \*   \*   \*   \*